United States Patent
Nebolsin et al.

(10) Patent No.: US 9,730,915 B2
(45) Date of Patent: Aug. 15, 2017

(54) METHOD FOR PREVENTING OR TREATING DISEASES ASSOCIATED WITH A REDUCED DENSITY OF INTERFERON RECEPTORS

(71) Applicant: OBSCHESTVO S OGRANICHENNOI OTVETSTVENNOSTIYU ("PHARMENTERPRISES"), Moscow (RU)

(72) Inventors: Vladimir Evgenievich Nebolsin, Moscow (RU); Andrei Yurievich Egorov, St. Petersburg (RU)

(73) Assignee: OBSCHESTVO S OGRANICHENNOI OTVETSTVENNOSTIYU "PHARMENTERPRISES", Moscow (RU)

( * ) Notice: Subject to any disclaimer, the term of this patent is extended or adjusted under 35 U.S.C. 154(b) by 0 days.

(21) Appl. No.: 14/915,475

(22) PCT Filed: Sep. 1, 2014

(86) PCT No.: PCT/RU2014/000656
§ 371 (c)(1),
(2) Date: Feb. 29, 2016

(87) PCT Pub. No.: WO2015/034400
PCT Pub. Date: Mar. 12, 2015

(65) Prior Publication Data
US 2016/0354345 A1 Dec. 8, 2016

(30) Foreign Application Priority Data
Sep. 3, 2013 (RU) .................. 2013140758

(51) Int. Cl.
*A61K 31/417* (2006.01)
*A61K 9/00* (2006.01)
(Continued)

(52) U.S. Cl.
CPC .......... *A61K 31/417* (2013.01); *A61K 9/0019* (2013.01); *A61K 9/0031* (2013.01);
(Continued)

(58) Field of Classification Search
CPC .. A61K 31/417; A61K 9/0019; A61K 9/0031; A61K 9/0034; A61K 9/2009;
(Continued)

(56) References Cited

FOREIGN PATENT DOCUMENTS

| EP | 1020179 A2 | 7/2000 |
|---|---|---|
| EP | 2433622 A2 | 3/2012 |
| WO | 2010134851 | 11/2010 |

OTHER PUBLICATIONS

Schafer et al. Drug Discovery Today 2008, 13 (21/22), 913-916.*
(Continued)

*Primary Examiner* — Savitha Rao
(74) *Attorney, Agent, or Firm* — Banner & Witcoff, Ltd.

(57) ABSTRACT

The invention relates to medicine, in particular, to a method for preventing and/or treating a disease associated with a reduced density of interferon receptors, the method comprising administering an effective amount of glutaryl histamine or a pharmaceutically acceptable salt thereof. Said disease may be hepatitis B, herpes, papilloma virus infection, or multiple sclerosis. The invention also relates to a pharmaceutical composition for prevention and/or treatment of diseases associated with a reduced density of interferon receptors, wherein the composition comprises an effective amount of glutaryl histamine or a pharmaceutically acceptable salt thereof. The invention solves a problem of providing a novel agent effective for overcoming a resistance to
(Continued)

interferon therapy in diseases selected from the group including hepatitis B, herpes, papilloma virus infection, or multiple sclerosis.

11 Claims, 3 Drawing Sheets

(51) Int. Cl.
*A61K 9/20* (2006.01)
*A61K 9/48* (2006.01)
(52) U.S. Cl.
CPC .......... *A61K 9/0034* (2013.01); *A61K 9/2009* (2013.01); *A61K 9/2013* (2013.01); *A61K 9/2018* (2013.01); *A61K 9/2059* (2013.01); *A61K 9/485* (2013.01); *A61K 9/4825* (2013.01); *A61K 9/4858* (2013.01); *A61K 9/4866* (2013.01)
(58) Field of Classification Search
CPC .. A61K 9/2013; A61K 9/2018; A61K 9/2059; A61K 9/4825; A61K 9/485; A61K 9/4858; A61K 9/4866
See application file for complete search history.

(56) References Cited

OTHER PUBLICATIONS

Horig et al. Journal of Translational Medicine 2004, 2(44).*
Heller et al. (Virology, 344, 2006 pp. 119-130).*
Konstatinov D et al. (primenenie dikarbamina V lechenii bolnykh khronicheskim gepatitom S. Rossiiskiii zhurnal gastroenterologii gepatologii, Kolproktologii, 2011, pp. 58-63).*
International Search Report for PCT/RU2014/000656, mailed Dec. 8, 2014, 2 pages.
Huangfu et al., "Cigarette smoking products suppress anti-viral effects of Type 1 interferon via phosphorylation-dependent downregulation of its receptor," FEBS Letters, 582(21-22), 3206-10, 2008.
Qian et al., "Pathogen Recognition Receptor Signaling Accelerates Phosphorylation-Dependent Degradation of IFNAR," PLoS Pathogens 7, pp. 1-13, 2011.

* cited by examiner

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
cactgactgt atattgtgtg aaagccagag                                    30

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
catctatact ggaagaaggt ttaagtgatg                                    30

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
atttccggtc catcttatca t                                             21

<210> SEQ ID NO 4
<211> LENGTH: 20
<212> TYPE: DNA
```

```
<213> ORGANISM: Artificial Sequence
<220> FEATURE:
<223> OTHER INFORMATION: primer

<400> SEQUENCE: 4
actgaacaac gttgtgttcc                                                    20
```

METHOD FOR PREVENTING OR TREATING DISEASES ASSOCIATED WITH A REDUCED DENSITY OF INTERFERON RECEPTORS

This application incorporates by reference the contents of a 1.1 kb text file created on Aug. 24, 2016 and named "14915475sequencelisting.txt," which is the sequence listing for this application.

FIELD OF THE INVENTION

The invention relates to medicine, in particular, to the use of glutaryl histamine or a pharmaceutically acceptable salt thereof for the prevention or treatment of diseases associated with a reduced density of interferon receptors.

BACKGROUND

Type I interferon, including interferon α (IFNα) and interferon β (IFNβ), are the most important factors of innate immunity responsible for protection of an organism from a viral infection and tumor growth. These cytokines perform their signal function by interacting with one receptor on a cell surface. The receptor is a heterodimer consisting of two chains IFNAR1 and IFNAR2. The interaction of interferons with the receptor results in activation of biochemical chains, starting with activation of Janus-kinases Tyk2 and Jak1 that provide phosphorylation of signal transducers and transcription activators Stat1 and Stat2. The latter molecules provide transcription of interferon-stimulated genes encoding antiviral effector proteins.

Interferon signals are powerful stimuli altering homeostasis, function and division of various interferon receptor-containing cells in the organism. Uncontrolled interaction of interferon molecules with receptors may have a toxic, damaging action on cells of the immune system and the whole organism. For example, a defect in the interferon-signaling pathway results in the development of pathology, such as systemic lupus erythematosus. In this connection, the intensity of interferon signaling is under strict control involving various mechanisms and, first of all, modulation/reduction in the density of interferon receptors on a cell surface (Coccia E. M., Uze G., Pellegrini S. (2006) Negative regulation of type I interferon signaling: facts and mechanisms. Cell Mol Biol (Noisy-le-grand) 52: 77-87). This physiological mechanism includes phosphorylation, ubiquitination, endocytosis, and subsequent degradation of a receptor subunit IFNAR1 in cell proteasomes (Kumar K. G., Krolewski J. J., Fuchs S. Y. (2004) Phosphorylation and specific ubiquitin acceptor sites are required for ubiquitination and degradation of the IFNAR1 subunit of type I interferon receptor. J Biol. Chem 279: 46614-46620).

Viruses use this physiological mechanism for their own benefit by reducing the intensity of interferon signaling, including by means of degradation of interferon receptors. The action of pathogens can include a directed suppression of interferon receptors with viral proteins. For example, hepatitis B virus reduces the density of interferon receptors with protein X (Cho I. R., Oh M., Koh S. S., Malilas W., Srisuttee R., Jhun B. H., Pellegrini S., Fuchs S. Y., Chung Y. H. Hepatitis B virus X protein inhibits extracellular IFN-α-mediated signal transduction by downregulation of type I IFN receptor. Int J Mol Med. 2012 April; 29(4):581-6. doi: 10.3892/ijmm.201.2.879. Epub 2012 Jan. 3). Other viruses, including herpes viruses, reach an effect of a reduction in the density of interferon receptors through cellular stress induced by the viruses (Liu J., HuangFu W. C., Kumar K. G. et al. Virus-induced unfolded protein response attenuates antiviral defenses via phosphorylation-dependent degradation of the type I interferon receptor. Cell Host Microbe 2009; 5:72-83). For example, herpes simplex viruses are able to reduce effectively the density of interferon receptors by degradation of their first subunit IFNAR1. (Qian j., Zheng H., Huangfu W. C., Liu j., Carbone C. J., Lou N. A., Baker D. P., Fuchs S. Y. Pathogen recognition receptor signaling accelerates phosphorylation-dependent degradation of IFNAR1. PLoS Pathog. 2011 June; 7(6):e1002065. doi: 10.1371/journal.ppat.1002065. Epub 2011 Jun. 9). It is known that the herpes virus family is represented by eight types of herpes viruses causing in humans diseases of various severity. The diseases are characterized in that the viruses are in a human body in their latent state.

A similarity in the genome structure of various herpes viruses provides common mechanisms of blocking interferon signaling.

Another example of viral modulation of interferon receptors in a viral infection is a disturbance in the balance between the interferon receptor subunits in papillomavirus oncogenesis in women (Tirone N. R., Peghini B. C., Barcelos A. C., Murta E. F., Michelin M. A. Local expression of interferon-alpha and interferon receptors in cervical intraepithelial neoplasia. Cancer Immunol Immunother. 2009 December: 58(12):2003-10. doi:10.1007/s00262-009-0707-6. Epub 2009 Apr. 18. PubMed PMID: 19381629).

Thus, acute and chronic viral infections are accompanied by interferon system suppression caused, inter alia, by accelerated degradation of interferon receptors (Qian J., Zheng H., Huangfu W. C., Liu J., Carbone C. J., Leu N. A., Baker D. P., Fuchs S. Y. Pathogen recognition receptor signaling accelerates phosphorylation-dependent degradation of IFNAR1. PLoS Pathog. 2011 June; 7(6):e1002065. doi: 10.1371/journal.ppat.1002065. Epub 2011 Jun. 9; 2008 Jun. 15; 197(1):54-62).

Chronic intoxications of an organism, for example, tobacco smoking, lead to a reduction in the density of interferon receptors in respiratory tract cells, thus resulting in an increased incidence of viral diseases in smokers and, probably, in a risk of lung cancer (Huang Fu W. C., Liu J., Harty R. N., Fuchs S. Y. Cigarette smoking products suppress anti-viral effects of Type I interferon via phosphorylation-dependent downregulation of its receptor. FEBS Lett. 2008 Sep. 22; 582(21-22):3206-10; Picaud S, Bardot B, De Maeyer E, Seif I. Enhanced tumor development in mice lacking a functional type I interferon receptor. J Interferon Cytokine Res. 2002 April; 22(4):457-62).

Currently, diseases accompanied by interferon system suppression are treated with recombinant (exogenous) interferon drugs. In that case, a reduced sensitivity of damaged cells to exogenous interferon is compensated with high doses of a drug. This results in toxic effects caused by interferon therapy, in particular, with the development of depressive syndromes (Patten S. B. Psychiatric side effects of interferon treatment. Curr Drug Saf. 2006 May; 1(2):143-50. Review. PubMed PMID: 18690925). Resistance to the therapy is mainly determined by a reduced expression of interferon receptors. For example, a reduced level of synthesis of the mRNA subunit of interferon receptor IFNAR1 observed in multiple sclerosis results in a reduced efficiency of therapy with interferon β (Serana F., Sottini A., Ghidini C., Zanotti C., Capra R., Cordioli C., Caimi L., Imberti L. Modulation of IFNAR1 mRNA expression in multiple sclerosis patients. J Neuroimmunol. 2008 Jun. 15; 197(1):54-62).

The same is observed in interferon therapy of chronic viral diseases. Virus-infected cells, losing a certain amount of interferon receptors, become non-sensitive to interferon therapy. For example, an effect of therapy with interferon-alpha in hepatitis B is often short-lived, and the disease passes to the stage of exacerbation accompanied by a rise in viral genome copies in the human blood. This means that a part of virus-infected cells in the organism did not respond to interferon therapy. For the same reason, interferon drugs do not heal a chronic infection caused by various herpes viruses (Kroeker A. L., Coombs K. M. Systems biology unravels interferon responses to respiratory virus infections. World J Biol. Chem. 2014 Feb. 26; 5(1):12-25. doi: 10.4331/wjbc.v5.i1.12. Review. PubMed PMID: 24600511; PubMed Central PMCID: PMC3942539); (Eron L. J., Toy C., Salsitz B., Scheer R. R., Wood D. J., Nadler P. I. Therapy of genital herpes with topically applied interferon. Antimicrob Agents Chemother. 1987 July; 31(7):1137-9. PubMed PMID: 3310870; PubMed Central PMCID: PMC174885).

The present inventors have unexpectedly found that an effective method for treating diseases accompanied by a reduced sensitivity of cells to interferon is a therapy directed to an increase in the density of interferon receptors on a cell surface. In this case, sensitization of cells to endogenous interferon signals can result in a therapeutic effect without the use of the preparations of a recombinant interferon or can provide a reduction of its therapeutic doses.

Currently, there is no agent capable of recovering or increasing the density of interferon receptors in case of their degradation in various pathological conditions. The present inventors have unexpectedly found that glutaryl histamine leads to an increased synthesis of the messenger RNAs of interferon receptors and an increased density of the receptors as such on a cell surface. Thus, glutaryl histamine is capable of recovering and/or increasing the density of interferon receptors on a cell surface, which makes this agent promising for prevention or treatment of a number of diseases. This agent can be used as monotherapy of viral diseases to achieve an effect of an increased sensitivity of cells to a low level of endogenous interferon because of a rise in the density of interferon receptors on a cell surface. In addition, glutaryl histamine can be used in complex therapy with interferon drugs to increase a response of immunosuppressed cells to an exogenous interferon.

SUMMARY OF THE INVENTION

The present inventors have shown in experiments that glutaryl histamine can be used in prevention and treatment of diseases associated with a reduced density of interferon receptors. Said diseases are, in particular, hepatitis B, herpes, papillomavirus infection, and multiple sclerosis. In administration of glutaryl histamine, the sensitivity of cells to the action of endogenous interferon is enhanced because of a rise in the density of interferon receptors on a cell surface, thereby overcoming virus-induced immunosuppression and providing a therapeutic effect in viral infections, such as herpes types 1-8, hepatitis B, papillomavirus infection, and multiple sclerosis. In addition, in the above-mentioned diseases, a resistance to interferon therapy is also overcome.

It has been established that a therapeutic effect of glutaryl histamine is not accompanied by toxic reactions and other side effects. In addition, glutaryl histamine, which is a low-molecular weight substance, cannot result in the formation of neutralizing antibodies.

In view of the above, the present invention relates to an agent for prevention and/or treatment of diseases associated with an increased density of interferon receptors, wherein the agent is glutaryl histamine of the following formula:

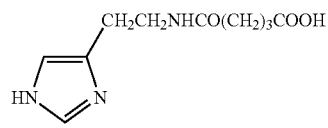

The invention also relates to a method for preventing or treating diseases associated with a reduced density of interferon receptors, the method comprising administering an effective amount of glutaryl histamine or a pharmaceutically acceptable salt thereof.

The prevention of the above-indicated diseases comprises prevention of a recurrence or exacerbation of said diseases.

Further, the invention relates to a pharmaceutical composition for prevention or treatment of diseases associated with a reduced density of interferon receptors, wherein the composition comprises an effective amount of glutaryl histamine or a pharmaceutically acceptable salt thereof.

In addition, the invention relates to a kit for prevention or treatment of diseases associated with a reduced density of interferon receptors, wherein the kit comprises the above-indicated composition and instructions for use thereof.

Further, the invention relates to use of glutaryl histamine or a pharmaceutically acceptable salt thereof for prevention or treatment of diseases associated with a reduced density of interferon receptors.

In addition, the invention relates to use of glutaryl histamine or a pharmaceutically acceptable salt thereof in the manufacture of a pharmaceutical composition for prevention or treatment of diseases associated with a reduced density of interferon receptors.

The diseases preferably can be selected from the group including hepatitis B, herpes (in particular, caused by herpes virus type 1, 2, 3, 4, 5, 6, 7, or 8), papilloma virus infection, and multiple sclerosis.

The above-indicated prevention or treatment is based on compensation of a reduced level of the expression of interferon receptors during a long-term therapy with interferon. Said prevention or treatment can be carried out by overcoming a resistance to interferon therapy in diseases selected from the group including hepatitis B, herpes, papilloma virus infection, and multiple sclerosis.

In a specific embodiment, the prevention and treatment are performed by increasing density of interferon receptors in multiple sclerosis by carrying out a therapy with interferon β. In addition, the invention relates to prevention of tobacco smoking-induced immunosuppression associated with a degradation of interferon receptors in smokers, wherein said treatment may be directed to overcoming a resistance to interferon therapy in smokers. Interferon receptors according to the invention are interferon α (IFNα) and interferon β (IFNβ) receptors.

Glutaryl histamine is preferably administered in a solid dosage form.

Glutaryl histamine or salts thereof may be administered to a patient in doses of from 0.1 to 100 mg/kg of human body weight per day, preferably in doses of from 0.1 to 30 mg/kg, more preferably in doses of from 0.3 to 30 mg/kg, when administered one or more times a day. A single dose of glutaryl histamine can be about 100 mg. The duration of the administration of glutaryl histamine may be from 5 days to 12 months.

Pharmaceutically acceptable salts of glutaryl histamine according to the invention may be salts thereof with alkali or alkaline-earth metals, preferably sodium, potassium, and lithium salts.

Glutaryl histamine or salts thereof are administered in an effective amount to provide a desired therapeutic result.

It should be noted that a specific dose for a particular patient depends on many factors, such as patient's age, body weight, gender, general health condition, and diet; the schedule and route of administration of the agent, the rate of excretion thereof from the body; and the severity of a disease in an individual under treatment.

The pharmaceutical compositions of the invention comprise glutaryl histamine or a pharmaceutically acceptable salt thereof in an effective amount required for a desired result, and may be prepared as unit dosage forms (for example, in solid, semi-solid, or liquid forms) comprising glutaryl histamine or a salt thereof as an active agent in a mixture with a carrier or an excipient suitable for intramuscular, intravenous, oral, sublingual, inhalation, intranasal, intrarectal, and transdermal administration. The active agent may be comprised in the composition together with conventional nontoxic pharmaceutically acceptable carriers suitable for the manufacture of solutions, tablets, pills, capsules, dragee, suppositories, emulsions, suspensions, ointments, gels, patches, and any other dosage forms.

Excipients can be various substances, such as saccharides, for example, glucose, lactose, or sucrose; mannitol or sorbitol; cellulose derivatives; and/or calcium phosphates, for example, tricalcium phosphate or calcium hydrophosphate. Compounds used as binders include starch paste (for example, corn, wheat, rice, or potato starch), gelatin, tragacanth, methylcellulose, hydroxypropylmethylcellulose, sodium carboxymethylcellulose, and/or polyvinylpyrrolidone. Disintegrants may be used, if necessary, and may include the aforementioned starches and carboxymethylstarch, crosslinked polyvinylpyrrolidone, agar-agar, or alginic acid or a salt thereof, such as sodium alginate.

Additives that may be optionally used are flowability control agents and lubricants, such as silicon dioxide, talc, stearic acid and salts thereof, such as magnesium stearate or calcium stearate, and/or propylene glycol.

Stabilizers, thickening agents, colorants, and fragrances also may be used as additives.

As an ointment base, there are suitable hydrocarbon ointment bases, such as white Vaseline and yellow Vaseline (Vaselinum album and Vaselinum flavum, respectively), Vaseline oil (Oleum Vaselini), and white ointment and liquid ointment (Unguentum album and Unguentum flavum, respectively), wherein solid paraffin or wax can be used as an additive providing a firmer texture; absorptive ointment bases, such as hydrophilic Vaseline (Vaselinum hydrophylicum), lanoline (Lanolinum), and cold cream (Unguentum leniens); water-removable ointment bases, such as hydrophilic ointment (Unguentum hydrophylum); water-soluble ointment bases, such as polyethylene glycol ointment (Unguentum Glycolis Polyaethyleni); bentonite bases; and others.

A base for gels may be selected from methylcellulose, sodium carboxymethylcellulose, oxypropylcellulose, polyethylene glycol or polyethylene oxide, and carbopol.

A base for suppositories can be a water-insoluble base such as cocoa butter; a water-soluble or water-miscible base, such as gelatin-glycerol or polyethylene oxide; or a combined base, such as a soap-glycerol base.

The amount of an active agent used in combination with a carrier can vary in the process of preparing a unit dosage form, depending on a recipient under the treatment and on a particular route of administration of a therapeutic agent.

For example, when glutaryl histamine or a salt thereof is used in the form of solutions for injection, the active agent therein is in an amount of 0.1 to 5%. A diluent may be selected from a 0.9% sodium chloride solution, distilled water, a Novocain solution for injection, Ringer's solution, a glucose solution, and specific solubilizing adjuvants. When glutaryl histamine or a salt thereof is administered in the form of tablets or suppositories, its amount is 10 to 300 mg per unit dosage form.

The dosage forms of the present invention are manufactured by routine procedures, such as blending, granulation, forming pills, dissolution, and lyophilization.

It should be noted that a long-term administration of glutaryl histamine or a salt thereof in therapeutic doses or doses greater by an order of magnitude than the therapeutic ones has not demonstrated adverse side effects.

EMBODIMENTS OF THE INVENTION

The invention is described below in more details with examples supporting the efficiency of glutaryl histamine for prevention and treatment of diseases according to the present invention, wherein the disclosed examples are not intended to limit the scope of the invention.

Example 1

Level of mRNA Synthesis of Interferon Receptors Under Action of Glutaryl Histamine A continuous cell line A-549 was treated with glutaryl histamine at a concentration of 100 ng/mL. The amount of messenger RNA copies of interferon receptors was determined by Real Time PCR analysis 16 hours after the treatment. The RNAs were isolated by using RNEASY® Kit (Qiagen). The RNA preparation was treated with DNAase (RNase-free DNaseI (Ambion). Reverse transcription was performed by using THERMOSCRIPT™ RT-PCR System (Invitrogen). Quantitative PCR was carried out with the primers:

```
Ifnar1 (forward)
5' CACTGACTGTATATTGTGTGAAAGCCAGAG 3', (reverse)
5' CATCTATACTGGAAGAAGGTTTAAGTGATG 3';
```

```
-continued
Ifnar2 (forward)
5' ATTTCCGGTCCATCTTATCAT 3', (reverse)
5'ACTGAACAACGTTGTGTTCC 3'.
```

Figure 1:
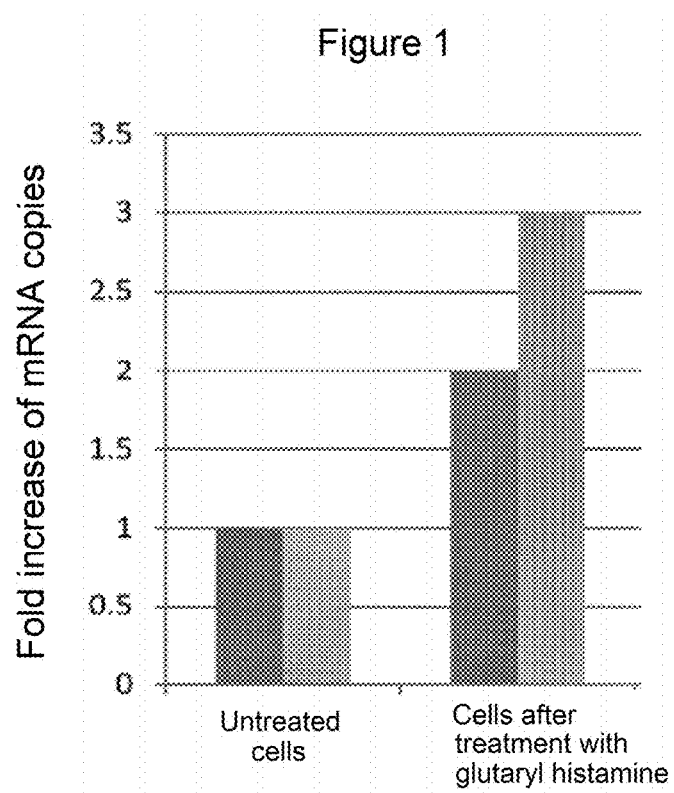
FIG. 1 is a diagram illustrating an increase in the synthesis of the mRNA subunits of interferon receptors under action of glutaryl histamine in epithelial cells A549.

Results. As can be seen on the graph (see FIG. 1), the treatment of cells with glutaryl histamine resulted at least in a two-folded increase in the mRNA synthesis of subunit IFNAR1 and a three-fold increase in the amount of the mRNA of subunit IFNAR2 of type I interferon receptor.

Example 2

Effect of Glutaryl Histamine on the Density of Interferon Receptors on the Surface of Primary Human Macrophages A 10-day primary culture of human macrophages in 96-well plates was incubated for 24 hours in the presence of glutaryl histamine at concentrations: 0.1, 1.0, 10 or 100 ng/mL or without it. Then, the cells were fixed with a paraformaldehyde solution (without permeabilization), the fixed cells were washed off with a detergent-containing buffer solution (PBS-Tween), blocked with a solution of bovine serum albumin, and incubated with antibodies to the interferon receptor subunits IFNAR1 or IFNAR2. The preparation was visualized by staining with horseradish peroxidase-labeled secondary antibodies and adding a substrate. Optical density was measured using an ELISA spectrophotometer.

Figure 2:
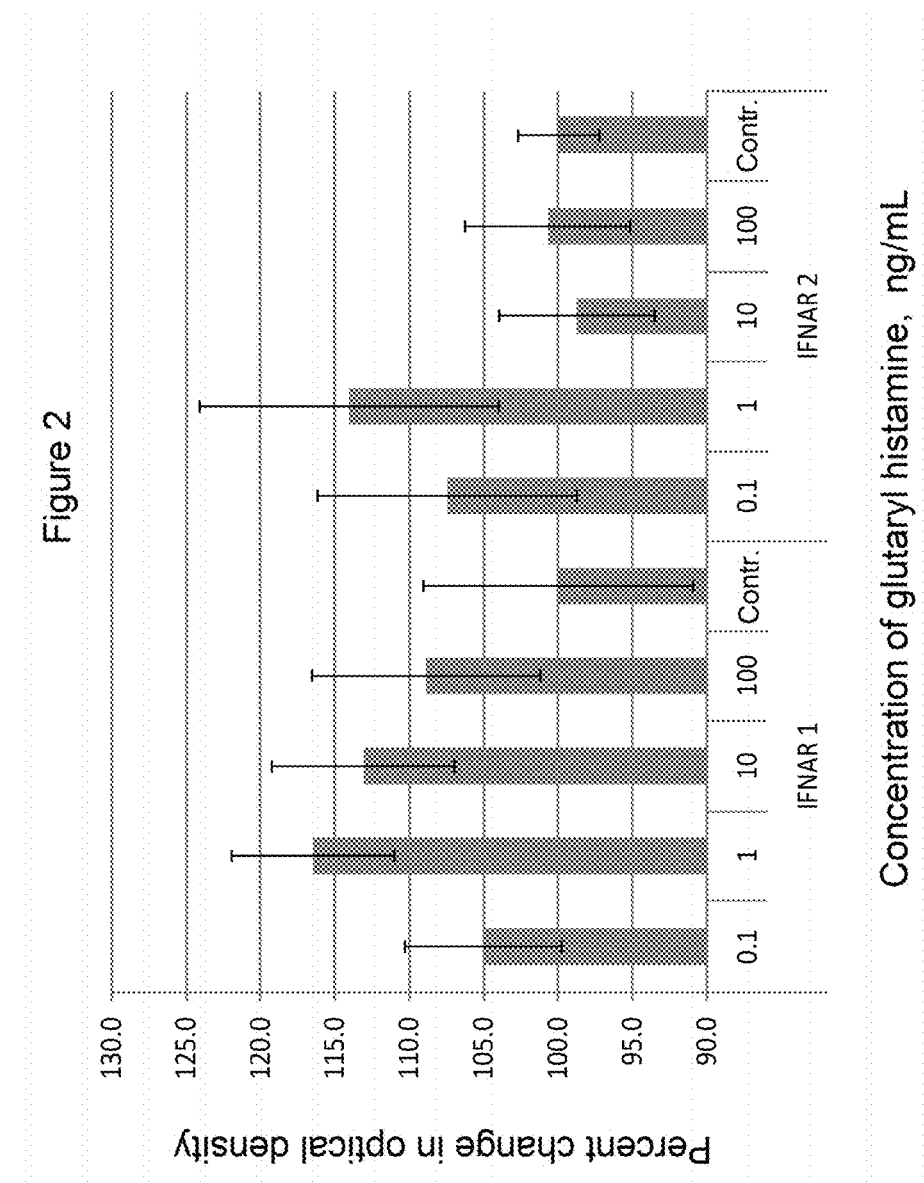
FIG. 2 is a diagram illustrating an increase in the protein amount of the interferon receptor subunits under action of glutaryl histamine on the surface of a primary culture of human macrophages.

As can be seen from this example (see FIG. 2), the treatment of macrophages with glutaryl histamine increased the density of two chains of interferon receptors on the cell surface, which is reflected in a noticeably increased level of the signal in staining with antibodies specific to IFNAR2 and IFNAR1.

Example 3

Effect of Glutaryl Histamine on Cell Sensitivity to Interferon

An increase in the density of interferon receptors on a cell surface must result in an increased sensitivity of cells to weak signals of endogenous interferon under conditions when its signaling is suppressed by a viral infection. In order to demonstrate an effect of sensitization of cells to interferon signals, cells A-549 were treated with glutaryl histamine at a concentration of 100 ng/mL and incubated for 8 or 24 hours before the cells were undergone to lysis in the presence or absence of 1 IU interferon-alpha (IFNα: ROF-ERON-A3®, Roche Molecular Biochemicals, Mannheim). Cell lysates were undergone to the procedure of immunoblot analysis (western blotting) by using monoclonal antibodies against to protein MxA (sc-50509, Santa Cruz Biotechnology) to stain membranes by a chemiluminescence method using a substrate (chemiluminescent reagent SUPER SIGNAL® West Femto Chemiluminescent Substrate (Thermo Fisher Scientific)). The protein MxA was selected as an indicator product that is indicative of the expression of interferon-stimulated genes (ISGs) when the cells are treated with interferon.

Figure 3:
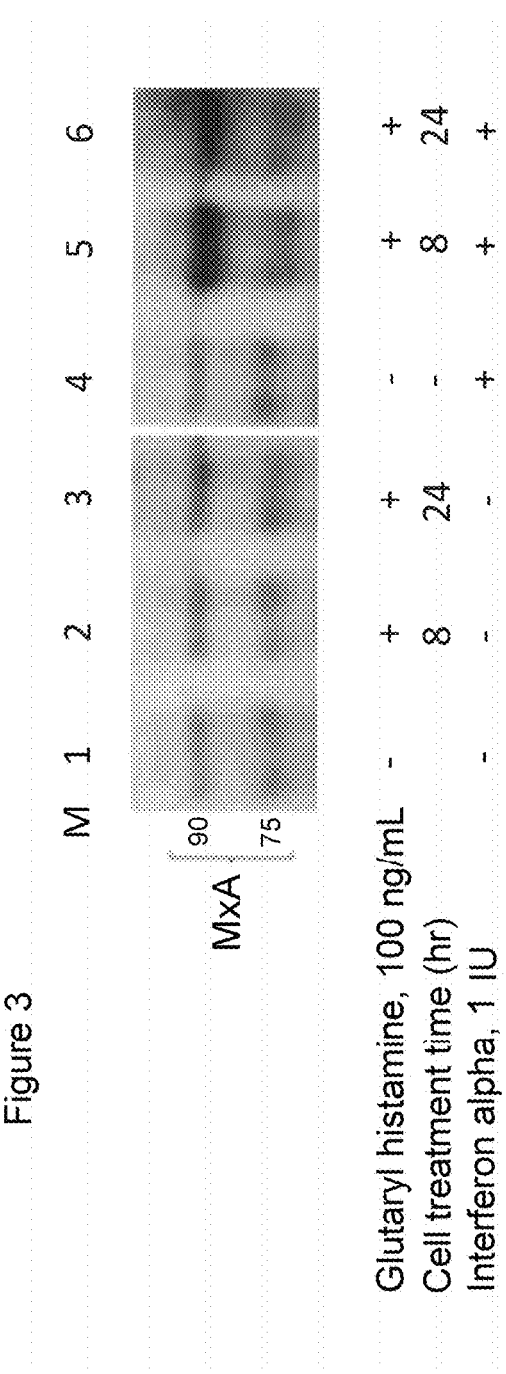
FIG. 3 is an immunoblot photograph demonstrating an effect of sensitization of glutaryl histamine-treated cells to low concentrations of interferon.

As can be seen from this example see FIG. 3), glutaryl histamine did not cause the accumulation of the antiviral MxA protein (lines 1, 2, and 3) in the cells that were not treated with interferon. Interferon, at a low concentration of 1 IU, also did not induce the synthesis of the MxA protein (line 4). At the same time, the cells that were treated with both glutaryl histamine and interferon showed an increased synthesis of the MxA protein already 8 hours after the incubation (line 5) and 24 after the beginning of the treatment of cells (line 6). Thus, the treatment of cells with glutaryl histamine resulted in an increased interferon signaling and, as a consequence, to an increased biosynthesis of antiviral effector molecules.

Example 4

Therapeutic Efficiency of Glutaryl Histamine in a Murine Model of Herpes Meningoencephaltitis Mice were intracerebrally infected with herpes simplex virus HSV-1/CL and HSV-2/VN in a dose of 30 µl comprising 10 $LD_{50}$.

A therapeutic effect of glutaryl histamine was studied by once-daily oral administration of 200 µl of the drug to the infected mice at a dose of 30 mg/kg 24, 48, 72, 96, and 120 hours after infection with the virus. Mice of the control group were administered placebo under the same conditions (200 ml of a physiological solution). The animals were monitored for 14 days after infection, and fatal cases among mice from herpes meningocephalitis were registered in the treated and control groups. Activity of the drug was evaluated by comparing mortality rates of animals treated with glutaryl histamine relative to animals of the control group. A reduction in the mortality rate of the treated animals relative to the control was expressed in percentage.

Indexes of death protection and life expectancy of the treated, control (infected animals untreated with glytaryl histamine), and intact (negative control) mice are given in Table 1.

The treatment of HSV-1/CL viral infection with glutaryl histamine showed a statistically significant reduction (p=0.02) in the mortality rate (from 95% down to 65%) and an increase in the average life expectancy (from 4.8 up to 8.1 days). Similarly, the treatment of HSV-2/VN-infected mice with glutaryl histamine led to a statistically significant reduction (p=0.008) in the mortality rate (from 85% down to 45%) and an increase in the average life expectancy (from 6.1 up to 10.2 days). The statistical significance was estimated by a Log-rank Mantel-Cox test. Thus, it has been shown that glutaryl histamine is therapeutically effective in the treatment of herpes infection in mice.

TABLE 1

| Experimental group | Mortality rate, % | Protection index, % | Life expectancy, days M ± σ |
|---|---|---|---|
| HSV-1, strain CL | | | |
| glutaryl histamine (30 mg/mL) | 65.0* | 31.6 | 8.1 ± 4.9 |
| Control for HSV-1/CL | 95.0 | 0.0 | 4.8 ± 3.1 |
| HSV-2, strain KN | | | |
| glutaryl histamine, (30 mg/ml) | 45.0** | 47.1 | 10.2 ± 4.8 |
| Control for HSV-2/KN | 85.0 | 0.0 | 6.1 ± 4.3 |
| Negative control | 0.0 | 100.0 | 14 ± 0.0 |

*P = 0.02
**P = 0.008

Example 5

Preparation of Glutaryl Histamine Dosage Forms

Dosage forms of glutaryl histamine used according to the present invention are prepared by standard methods, such as, for example, processes of mixing, granulating, forming pills, dissolving and lyophilizing.

Tablet Form

A tablet form is prepared by using the following ingredients:

| | |
|---|---|
| Glutaryl histamine or a pharmaceutically acceptable salt thereof | 1-100 mg |
| Potato starch | 20-50 mg |
| Magnesium stearate | 3 mg |
| Aerosil | 1 mg |
| Lactose | up to 300 mg |

The ingredients are mixed and compressed to form tablets weighing 300 mg

Gelatinous Capsules

| | |
|---|---|
| Glutaryl histamine or a pharmaceutically acceptable salt thereof | 90 mg |
| Lactose (milk sugar), potato starch, colloidal silica (aerosi), magnesium stearate | amount required for a 220 mg capsule |

The above-mentioned ingredients are mixed and granulated, the resulting granules are placed into solid gelatinous capsules in an amount of 220 mg.

Suppositories

Example of the formulation of a suppository

| | |
|---|---|
| Glutaryl histamine or a pharmaceutically acceptable salt thereof | 1-100 mg |
| Cacao oil | amount required for a suppository |

Rectal, vaginal, and urethral suppositories can be optionally prepared with corresponding excipients.

Solution for Injection

Example of the formulation of a solution for injections:

| | |
|---|---|
| Glutaryl histamine or a pharmaceutically acceptable salt thereof | 1-100 mg |
| Water for injection | 2 ml |

A solution for injections can be prepared by using, as a diluent, a 0.9% sodium chloride solution, distilled water, or a novocain solution. Product forms are ampules, flasks, syringe-tubes, and "inserts".

---

The invention claimed is:

1. A method for increasing the density of interferon receptors upon treating a disease associated with a reduced density of interferon receptors, the method comprising administering an effective amount of glutaryl histamine or a pharmaceutically acceptable salt thereof.

2. The method of claim 1, wherein said disease is selected from the group consisting of hepatitis B, herpes, papilloma virus infection, and multiple sclerosis.

3. The method of claim 1, wherein said increase of the density of interferon receptors overcomes a resistance to therapy with interferon and/or compensates for a reduced expression level of interferon receptors in a long-term therapy with interferon.

4. The method of claim 1, wherein said disease is an immunosuppression from tobacco smoking, wherein the immunosuppression is associated with a degradation of interferon receptors in smokers.

5. The method of claim 1, wherein the interferon receptors are interferon α (IFNα) and/or interferon β (IFNβ) receptors.

6. The method of claim 1, wherein glutaryl histamine is administered in a solid dosage form, and a duration of the administration of glutaryl histamine is from 5 days to 12 months.

7. The method of claim 1, wherein the dose of glutaryl histamine or a pharmaceutically acceptable salt thereof is from 0.1 to 100 mg/kg of human body weight per day.

8. The method of claim 1, wherein a single dose of glutaryl histamine is 100 mg.

9. A method for increasing the density of interferon receptors upon treating a disease selected from the group consisting of hepatitis B, herpes, papilloma virus infection, and multiple sclerosis, the method comprising administering an effective amount of glutaryl histamine or a pharmaceutically acceptable salt thereof.

10. The method of claim 9, wherein glutaryl histamine is administered in a solid form, and a duration of the administration of glutaryl histamine is from 5 days to 12 months.

11. The method of claim 9, wherein the dose of glutaryl histamine or a pharmaceutically acceptable salt thereof is from 0.1 to 100 mg/kg of human body weight per day.

* * * * *